United States Patent [19]

Heinze et al.

[11] Patent Number: 4,870,967
[45] Date of Patent: Oct. 3, 1989

[54] MEASURING ARRANGEMENT FOR CONTROLLING AN IMPLANTABLE BODY-ASSIST DEVICE

[75] Inventors: Roland Heinze, Munich; Hans D. Liess, Muensing, both of Fed. Rep. of Germany

[73] Assignee: Siemens Aktiengesellschaft, Berlin and Munich, Fed. Rep. of Germany

[21] Appl. No.: 84,204

[22] Filed: Aug. 12, 1987

[30] Foreign Application Priority Data

Aug. 18, 1986 [DE] Fed. Rep. of Germany ....... 3627933

[51] Int. Cl.$^4$ ........................ A61N 1/00; H05G 00/00
[52] U.S. Cl. ............................... 128/419 PG; 128/734
[58] Field of Search ............ 128/421, 734, 422, 419 P, 128/419 PG, 419 D, 788, 784, 783

[56] References Cited

U.S. PATENT DOCUMENTS

| 4,406,288 | 9/1983 | Horwinski et al. | 128/788 |
|---|---|---|---|
| 4,688,574 | 8/1987 | Dufresne et al. | 128/421 |
| 4,688,575 | 8/1987 | DuVall | 128/788 |
| 4,721,110 | 1/1988 | Lampadius | 128/419 PG |
| 4,730,618 | 3/1988 | Lekholm et al. | 128/419 PG |
| 4,787,389 | 11/1988 | Tarjan | 128/419 PG |

FOREIGN PATENT DOCUMENTS 0096464 12/1983 European Pat. Off. ..... 128/419 PG

Primary Examiner—Francis Jaworski
Assistant Examiner—George Manuel
Attorney, Agent, or Firm—Hill, Van Santen, Steadman & Simpson

[57] ABSTRACT

An implantable arrangement for operating a body-assist device, the body-assist device including circuitry for generating electrical signals and also being implanted in a patient, includes circuitry for controlling the generation of the electric signals, a measuring probe in the patient for obtaining signals to be used by the control circuitry, a single current conductor electrically connecting the control circuitry and the measuring probe and forming a first current path therebetween, and spaced electrodes connected to the measuring probe and the control circuitry disposed in the patient with body tissue therebetween such that a second current path is formed in the body tissue.

13 Claims, 3 Drawing Sheets

MEASURING ARRANGEMENT FOR CONTROLLING AN IMPLANTABLE BODY-ASSIST DEVICE

BACKGROUND OF THE INVENTION

1. Field of the Invention

The present invention is directed to a measuring arrangement for operating and controlling an implantable body-assist device, and in particular to such an arrangement for operating and controlling a heart pacemaker having a pacing circuit which generates pulses, and a pulse control circuit to which a measuring probe is electrically connected via a conductor in a catheter.

2. Description of the Prior Art

Measuring devices are known in the art which acquire a signal corresponding to the blood oxygen concentration of the patient in which the measuring device is implanted. Such devices are used to control the frequency of pacing of a heart pacemaker as described, for example, in German patent No. 31 52 963. The schematic structure of such a known measuring device and pacemaker is shown in FIG. 1.

In this known pacing system, a heart pacemaker H includes a combined measuring and stimulation catheter 3, and a control stage 1 alternately connects the catheter 3 to a pacing circuit 9 or to an evaluation circuit 10, which controls operation of the pacing circuit 9. Two operating conditions of the system are possible by means of the control stage 1. Given switch position 1a, the pacing circuit 9 receives an ECG signal via an electrode 6 extending through the catheter 3 and an electrode 7, which is the housing of the heart pacemaker H. The pacing circuit 9 generates a stimulation pulse via the current conductor 3a and the electrodes 6 and 7. In switch position 1b of the control stage 1, the evaluation circuit 10 receives a signal from the measuring probe 2 via the current conductors 3a and b, and generates control signals for controlling the pacing circuit 9 based on the measurement signal.

In this known system, the catheter 3 must be bipolar, at least between the control stage 1 and the measuring probe 2. Bipolar catheters, however, are thicker and correspondingly less flexible, and have a higher failure rate, than single-pole catheters. Moreover, the manufacture of bipolar measuring catheters is more complicated and expensive than the manufacture of single-pole catheters.

SUMMARY OF THE INVENTION

It is an object of the present invention to provide a measuring arrangement for controlling and operating an implantable body-assist device wherein the catheter can be designed to be more flexible and reliable, and such that the manufacture thereof is more cost-beneficial.

It is a further object of the present invention to provide such a measuring arrangement suitable for use in implantable heart pacemakers.

The above objects are achieved in accordance with the principles of the present invention in a measuring arrangement wherein the catheter has a single current conductor electrically connecting the control stage and the measuring probe, and wherein the body tissue of the patient is used as a second current conductor between the measuring probe and the control stage by means of spaced electrodes implanted in the patient. At least one current line is thus eliminated in the catheter between the control stage and the measuring probe, so that the catheter is more flexible, more reliable, and less expensive to manufacture.

A measuring sensor in one embodiment can control the resistance of the measuring probe so that changes in the current flux through the overall measuring circuit (measuring probe and current lines) are dependent on the measured value, but are independent of resistance changes in the body tissue.

In one embodiment, the measuring sensor may be a variable resistor connected in the measuring circuit having a resistance change, dependent on the measured variable, which is extremely large in comparison to the resistance changes of the current conductors (which are unwanted variables) so that the changes in the value of the resistance of the body tissue are negligibly small within a defined measuring range.

In another embodiment for making the measured result independent of the resistance of the body tissue, the measuring sensor controls a constant current regulator connected in series in the measuring circuit.

The problem of suppressing the influence of resistance changes in the body tissue can also be solved in a further embodiment wherein the measuring probe reacts to a measuring pulse, transmitted by the control stage, with a change in resistance which includes a delay Δt in comparison to the measuring pulse, which is dependent on the measured value. This pulse-shaped change in resistance can be unambiguously acquired in comparison to the slow changes in the resistance of the body tissue.

In another embodiment, the measuring probe converts the measured value into a digitally coded pulse sequence in accordance with the changes in the resistance in the measuring probe. This digital information is similarly uninfluenced by the slow changes of the resistance in the measuring circuit.

If an analog frequency converter is used instead of an analog-to-digital converter, a further embodiment is useful wherein the resistance of the measuring probe is frequency-modulated and the measured value, as frequency information, can thus be transmitted independently of resistance changes in the body tissue.

In a measuring device for a heart pacemaker wherein the control stage additionally generates stimulation pulses as output signals to the heart muscle via a catheter having a stimulation electrode, a measuring probe can be connected in series with the line between the control stage and the stimulation electrode. In this embodiment the measuring probe contains a diode which conducts in the transmission direction for the stimulation pulses, and is non-conducting in the direction of transmission of the measuring pulses. The stimulation pulses are thus not attenuated by the resistance of the measuring probe, which is dependent on the measured variable.

In a measuring device wherein the control stage generates stimulation pulses through a capacitor which discharges in the stimulation phase via body resistance and which is subsequently re-charged in the depolarization phase, the current required for re-charging, which is part of the energy loss of the heart pacemaker, can be advantageously utilized for controlling the measuring probe by using the control stage to set the measuring pulse through the capacitor. The measuring pulse is transmitted in the opposite direction in comparison to the stimulation pulse.

DESCRIPTION OF THE PREFERRED EMBODIMENTS

Figure 2:
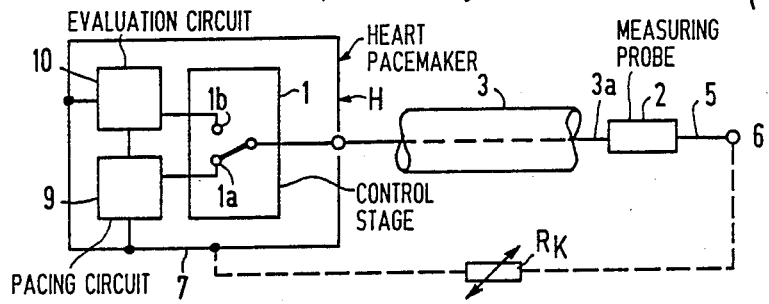
FIG. 2 is a schematic block diagram of a heart pacemaker and measuring arrangement constructed in accordance with the principles of the present invention.

A heart pacemaker H constructed in accordance with the principles of the present invention is schematically shown in FIG. 2. The pacemaker H includes a control stage 1 which alternately connects a catheter 3 to a pacing circuit 9 (which includes a pulse generator) or to an evaluation circuit 10. When in the switching position 1b, the evaluation circuit 10 is connected to a terminal of a measuring probe 2 integrated in the catheter 3 via a single-lead current conductor 3a disposed in the catheter 3. The second terminal of the measuring probe 2 is connected to a stimulation electrode 6 via a second section 5 of the same current conductor, which is also arranged in the catheter 3. Body tissue of the patient, referenced in the drawing by a variable body resistance $R_k$, and the pacemaker housing 7, functioning as an electrode, serve as a return conductor path to the heart pacemaker H. Stimulation pulses as well as measured values are thus transmitted through the current conductor 3a and 5, and through the body tissue, as indicated by the dashed line. The catheter 3 thus requires only one current conductor 3a, thus enhancing the flexibility and reliability thereof.

Figure 1:
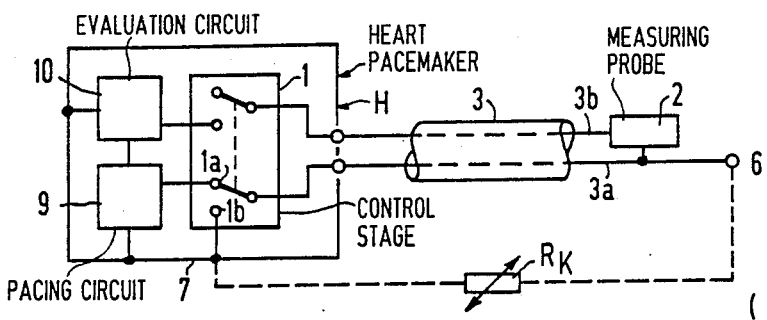
FIG. 1 is a schematic block diagram of a heart pacemaker and measuring arrangement as is known in the prior art.
Figure 3:
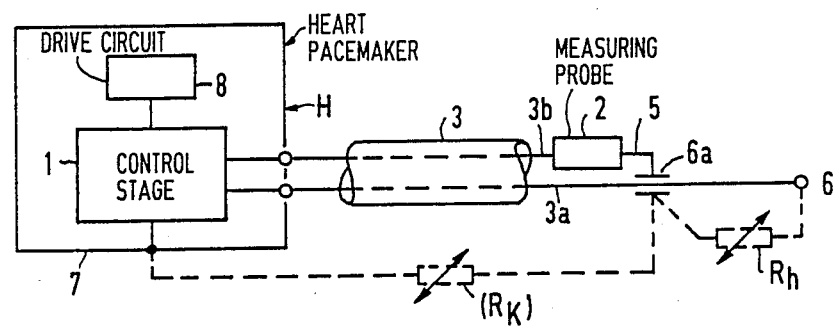
FIG. 3 is a schematic block diagram of a heart pacemaker and measuring arrangement constructed in accordance with the principles of the present invention.

A further embodiment for a measuring arrangement using body tissue as the return path for the measuring probe 2 is shown in FIG. 3. In this embodiment, the catheter 3 includes an indifferent or passive electrode 6a integrated therein in a known manner in addition to the stimulation electrode 6. Such passive electrodes are required if the stimulation pulses and ECG measurement signals are to be transmitted with a minimum of disturbances to the heart pacemaker H, and therefore these signals should not be transmitted through the body tissue, but rather are implemented in the heart itself between the stimulation electrode 6 and the passive electrode 6a. In this case, the current flux through the measuring probe 2 occurs via the lines 3b and 5 to the passive electrode 6a, and proceeds from the electrode 6a through the venous blood and the heart muscle tissue $R_h$ to the stimulation electrode 6, and is returned via the line 3a to the control stage 1. In this case, the catheter 3 does include a second conductor 3b, however this is still an advantage because the measuring probe 2 requires only two connections. If a similar arrangement were to be undertaken based on the prior art system shown in FIG. 1, three connections are required, namely two connections to the pacemaker H and a further connection to the stimulation electrode 6. Such connections, however, are complicated in the probe manufacture, and the failure probability is statistically increased by every connection.

In the embodiment of FIG. 3, the control stage 11, operated by a drive circuit 8, includes the necessary pacing and evaluation circuitry shown separately in FIG. 2.

Figure 4:
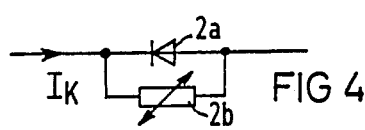
FIGS. 4 and 5 show different embodiments for a measuring probe constructed in accordance with the principles of the present invention.

One embodiment of a measuring probe 2 is schematically shown in FIG. 4. In this embodiment, a diode 2a and a measuring sensor in the form of a resistor 2b are connected in parallel. The resistance of the resistor 2b changes in accord with changes in the measured variable. For a temperature measurement, for example, the resistor 2b can be a temperature-dependent resistor. The diode 2a is polarized to be conductive for the stimulation pulse. Attenuation of the stimulation pulse due to a voltage drop across the resistor 2b is thus prevented. The measurement is undertaken by a resistance measurement using a constant current in the non-conducting direction of the diode 2a. In this simple embodiment, the greatest potential for disturbances arises due to fluctuating body resistance $R_K$, and due to the polarization voltage which arises with each stimulation pulse at the electrode 6. The influence of these disturbing factors, however, can be made negligibly low by making the resistance change of the resistor 2b, dependent on the measured variable high in comparison to the resistance changes of the connecting lines, including the body resistance $R_K$, which act as disturbing influences.

Figure 5:
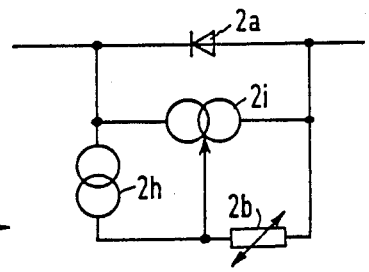

A further embodiment for eliminating the influence of disturbing factors, such as fluctuating body resistance $R_K$, is shown in FIG. 5. In this embodiment, the diode 2a is connected across a controllable current source 2i in the measuring probe 2. A second current source 2h supplies the resistor 2b, which changes resistance dependent on the measured variable. A control input of the current source 2i is connected to a junction of the current source 2h and the resistor 2b.

Figure 6:
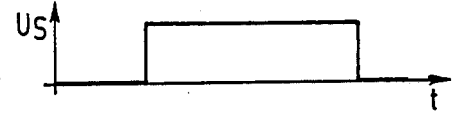
FIGS. 6, 7 and 8 are respectively voltage and pulse diagrams for explaining the operation of the measuring probe.
Figure 7:
Figure 8:
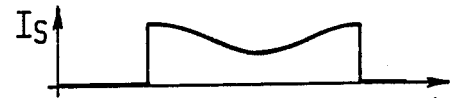

When charging the circuit of FIG. 5 with a measuring pulse $U_S$, as shown in FIG. 6, a constant current flows through the current source 2h and generates a control voltage $U_M$, shown in FIG. 7, which is dependent on the measured value at the resistor 2b. The control voltage $U_M$ controls the controllable current source 2i. On the basis of the control voltage $U_M$, the controllable current source 2i supplies a constant current $I_S$, as shown in FIG. 8, which is proportional to the control voltage $U_M$, and thus is proportional to the measured value. The constant current $I_S$ can be measured in the evaluation circuit 10. In a prescribable range, the constant current $I_S$ is independent of the resistance of the connecting lines including the body resistance $R_K$, and is also independent of the polarization voltage at the electrodes 6 and 7.

Figure 9:
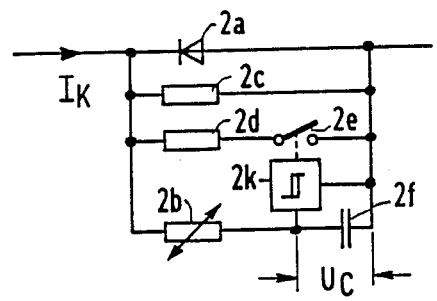
FIG. 9 is a schematic block diagram is a further embodiment of a measuring probe constructed in accordance with the principles of the present invention.
Figure 10:
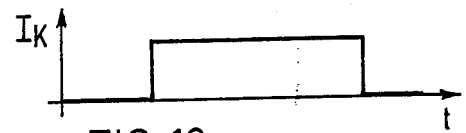
FIGS. 10, 11 and 12 are respectively current and voltage diagrams for explaining the operation of the circuit of FIG. 9.
Figure 11:

A further embodiment is shown in FIG. 9 for eliminating the influence of changing body resistance $R_K$ and the influence of polarization voltages. In this embodiment, the measuring probe reacts with a change in resistance to a measuring pulse $U_S$ emitted by the evaluation circuit 10, this change in resistance including a delay in comparison to the measuring pulse $U_S$ which is dependent on the measured value. As shown in FIG. 9, the diode 2a is connected across a resistor 2c and across a series-connected resistor 2d and a switch 2e. The diode 2a is also connected in parallel with the series connection of the variable resistor 2b, having a resistance which changes in dependence on the measured variable, and a capacitor 2f. The switch 2e is controlled through a threshold switch 2k by the voltage $U_C$ across the capacitor 2f. The operation of the circuit of FIG. 9 shall be described with reference to FIGS. 10–12. When the circuit is charged with a constant current measuring pulse $I_K$, as shown in FIG. 10, opposite the conducting direction of the diode 2a, the switch 2e remains open at the beginning of the pulse, and the total effective probe resistance $R_S$ of the measuring probe 2, shown in FIG. 11, is essentially defined by the resistor 2c.

Figure 12:
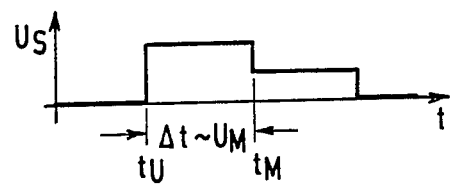

A measuring pulse $U_S$ is thus present across the measuring probe 2. At the same time, the capacitor 2f is charged via the resistor 2b in dependence on the measured variable. After a time $\Delta t$, which is dependent on the value of resistance of the resistor 2b, and thus on the measured variable, the voltage $U_C$ across the capacitor 2f reaches the threshold of the switch 2k, causing the switch 2e to close. The resistor 2d is thus cut into the circuit, so that the probe resistance $R_S$, and thus the voltage of the measuring pulse $U_S$, decrease. The time span $\Delta t$ between a beginning $t_U$ of the measuring pulse $I_K$ and a point in time $t_M$ of the voltage drop of the measuring pulse $U_S$ represents a measure for the measured variable which can be acquired independently of slow changes of the resistance $R_k$ of the body tissue, and independently of polarization voltages. This is indicated in FIG. 12.

Figure 13:
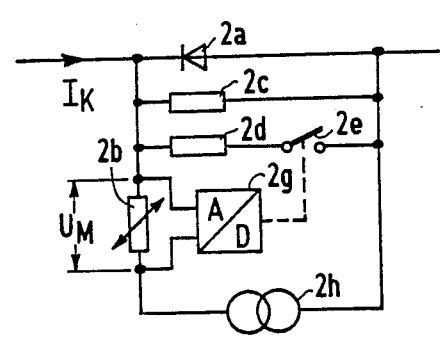
FIG. 13 is a digital embodiment of a measuring probe constructed in accordance with the principles of the present invention.

It is also possible to digitally transmit the measured variable independently of resistance fluctuations in the body tissue and independently of the polarization voltages. An exemplary embodiment for a digital measuring probe is shown in FIG. 13. In this embodiment, the diode 2a is again connected in parallel with a resistor 2c and with a series circuit consisting of a resistor 2d and a switch 2e. The diode 2a is also connected in parallel with a series circuit consisting of a resistor 2b, having a resistance which changes dependent on the measured variable, and a constant current source 2h. An analog-to-digital converter 2g converts the control voltage $U_M$, acquired across the resistor 2b and thus dependent on the measured value, and converts this signal into a digital value which is used to control operation of the switch 2e.

Figure 14:
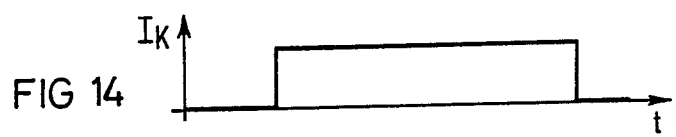
FIGS. 14, 15, 16 and 17 are respectively current and voltage diagrams for explaining the operation of the circuit of FIG. 13.
Figure 15:
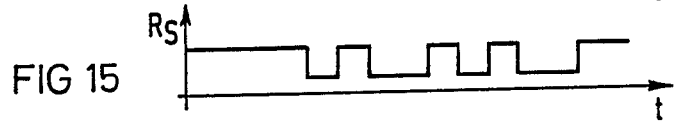
Figure 16:
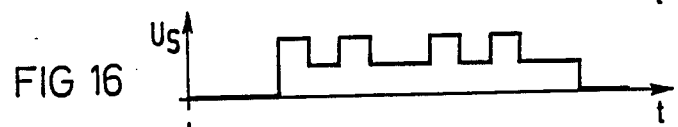
Figure 17:
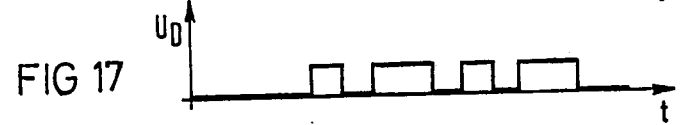
Figure 18:
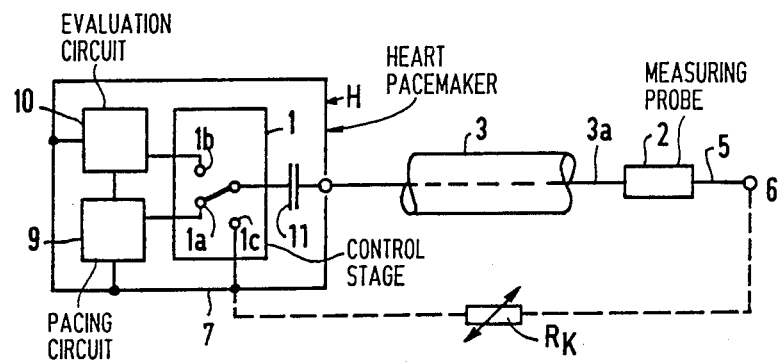
FIG. 18 is a schematic block diagram of a further embodiment of a measuring arrangement and heart pacemaker constructed in accordance with the principles of the present invention.

When the circuit of FIG. 13 is charged with a measuring pulse $I_K$, as shown in FIG. 14, opposite the conducting direction of the diode 2a, a measured value-dependent control voltage $U_M$ is present across the inputs of the converter 2g. This voltage is coded to form a digital signal which controls the switch 2e, and thus cuts the resistor 2d into the circuit. The digital information is therefore transmitted to the evaluation circuit 10 on the basis of the changes of the probe resistance $R_S$ (FIG. 15) or on the basis of the probe voltage $U_S$ (FIG. 16). The analog-to-digital converter 2g may be constructed such that it first generates a start pulse after every measuring pulse $I_K$, and then transmits the acquired measured value, for example in the form of binary information. Such a binary output signal is shown in FIG. 17. Another embodiment of a pacemaker and measuring arrangement constructed in accordance with the principles of the present invention is shown in FIG. 18, wherein the heart pacemaker H includes a capacitor 11 through which the stimulation pulse is conducted.

The single-pole catheter 3 of the invention permits the energy for recharging the capacitor 11, which is used in the stimulation circuit of the pacing circuit 9, to be used for making the measurement. This energy would be otherwise lost.

In comparison to the embodiment of FIG. 2, the control stage 1 includes a third position 1c for discharging any charge remaining in the capacitor 11 to ground after the measuring phase.

Figure 19:
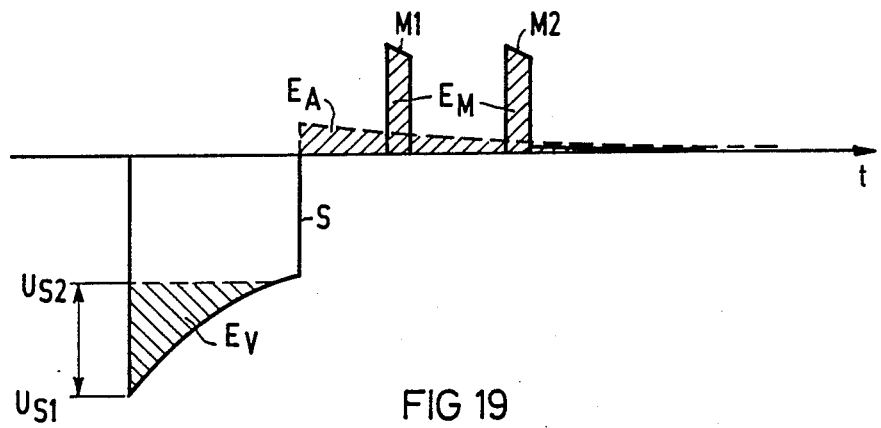
FIG. 19 is a voltage/time diagram for explaining the operation of the circuit of FIG. 18.

In FIG. 19, the stimulation pulse which is generated via the capacitor 11 is referenced S. The dissipated power $E_V$ contained in the voltage drop of the stimulation pulse S from $U_{S1}$ to $U_{S2}$ is normally compensated in the re-charging phase (dashed line) by discharging the capacitor 11 through the body resistance $R_K$. By means of an appropriate measuring pulse control, however, the charging power $E_A$ thereby required can be used, for example, for two measuring pulses $M_1$ and $M_2$, having the power consumption $E_M$.

Although modifications and changes may be suggested by those skilled in the art it is the intention of the inventors to embody within the patent warranted hereon all changes and modifications as reasonably and properly come within the scope of their contribution to the art.

We claim as our invention:

1. A measuring arrangement for operating a body-assist device having means for generating electrical signals and implanted in a patient, said measuring arrangement comprising:
   control means for forming control signals from a signal corresponding to a body variable of said patient for controlling said means for generating electrical signals;
   a measuring probe in said patient for obtaining said signals corresponding to a body variable of said patient for use by said control means in forming said control signals;
   a single current conductor means for electrically connecting said control means and said measuring probe and for forming a first current path therebetween; and
   electrode means connected to said measuring probe and to said control means and spaced so that body tissue of said patient is disposed therebetween and adapted for utilizing said body tissue as a second current path between said measuring probe and said control means.

2. A measuring arrangement as claimed in claim 1, wherein said measuring probe includes a measuring sensor having variable resistance, said variable resistance changing dependent on said body variable of said patient to be measured but being independent of the resistance of said body tissue.

3. A measuring arrangement as claimed in claim 1, wherein said control means includes means for generating a measuring pulse to said measuring probe having a duration and energy insufficient to trigger activity in said body tissue for use by said measuring probe in obtaining said signals corresponding to said body variable of said patient.

4. A measuring arrangement as claimed in claim 3, wherein said measuring pulse causes polarization voltages at said electrode means, and further comprising means for maintaining said second current path until said polarization voltages have dissipated.

5. A measuring arrangement as claimed in claim 1, wherein said measuring probe includes a variable resistor connected in series with said single current conductor means and said electrode means, and wherein said first and second current paths are subject to resistance changes, and said variable resistor changing resistance dependent on said body variable of said patient to be measured in an amount which is substantially greater than the resistance changes of said first and second current paths.

6. A measuring arrangement as claimed in claim 1, wherein said measuring probe includes a variable resistor having a resistance which changes dependent on said body variable to be measured, and a constant current regulator connected in series with said resistor.

7. A measuring arrangement as claimed in claim 1, wherein said control means generates a measuring pulse during a measuring phase, and wherein said measuring probe comprises:
a variable resistor which changes resistance value in dependence on said body to be measured; and
means for delaying said change in resistance of said variable resistor following said measuring pulse.

8. A measuring arrangement as claimed in claim 1, wherein said measuring probe comprises:
a variable resistor which changes resistance dependent on said body variable to be measured; and
means for generating a digital signal based on the change in resistance of said variable resistor.

9. A measuring arrangement as claimed in claim 1, wherein said measuring probe comprises:
a variable resistor having a resistance which changes dependent on said body variable to be measured; and
means for generating a signal having a parameter which changes in accordance with the changes in resistance of said variable resistor.

10. A measuring arrangement as claimed in claim 1, wherein said means for generating electrical signals generates a measurement pulse and a tissue stimulation pulse, wherein said measuring probe is connected in series with said single current conductor between said control means for and said electrode means, and wherein said measuring probe includes a diode having a conducting direction for said stimulation pulses and a nonconducting direction for for said measuring pulses.

11. A measuring arrangement as claimed in claim 1, wherein said means for generating electrical signals generates a tissue simulation pulse via said single current conductor means and said electrode means, and further comprising a capacitor connected between said control means and said single current conductor means, said capacitor discharging through said body tissue during said stimulation pulse, means in said control means connected to said capacitor for re-charging said capacitor after said stimulation pulse, and means in said control means for using part of the energy for re-charging said capacitor to generate a measuring pulse through said capacitor in a current direction opposite in direction to said stimulation pulse.

12. An arrangement for operating a body-assist device having means for delivering a therapeutic treatment to a patient, said arrangement and said device being implanted in said patient said arrangement comprising:
control means for forming control signals controlling said means for delivering;
means for obtaining signals for use by said control means for forming said control signals;
single conductor means mechanically and electrically connecting said means for controlling and said means for obtaining signals and forming a first current conducting path therebetween; and
means for forming a second current conducting path between said means for controlling and said means for obtaining signals adapted to include body tissue of said patient as part of said second current conducting path.

13. An arrangement for operating an implantable body-assist device, said body-assist device including means for generating a measurement pulse and means for generating a stimulation pulse and further including means for controlling said means for generating said stimulation pulse, said measuring arrangement comprising:
a single current conductor means for terminating in an electrode adapted for connection to body tissue;
a measuring probe connected in said single current conductor means to said electrode;
means for switching connection of said single current conductor means to said means for generating a measurement pulse or to said means for generating a stimulation pulse; and
a further electrode spaced from said electrode terminating said single current conductor means and connected to said means for controlling, said electrode and said further electrode being adapted for placement in the body of said patient with body tissue therebetween forming a further current path including said body tissue, in addition to said single current conductor means.

* * * * *